United States Patent
Alkharfy et al.

(10) Patent No.: US 10,463,632 B2
(45) Date of Patent: Nov. 5, 2019

(54) METHOD FOR TREATING A NEUROVASCULAR COMPLICATION OF DIABETES MELLITUS

(71) Applicant: KING SAUD UNIVERSITY, Riyadh (SA)

(72) Inventors: Khalid Mohammed Alkharfy, Riyadh (SA); Ghulam Mohammad, Riyadh (SA); Ajaz Ahmad, Riyadh (SA); Mohammad Mairaj Siddiquei, Riyadh (SA); Ahmed Abu El-Asrar, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/046,426

(22) Filed: Feb. 17, 2016

(65) Prior Publication Data
US 2017/0231925 A1    Aug. 17, 2017

(51) Int. Cl.
*A61K 31/122*    (2006.01)

(52) U.S. Cl.
CPC .................................. *A61K 31/122* (2013.01)

(58) Field of Classification Search
None
See application file for complete search history.

(56) References Cited

U.S. PATENT DOCUMENTS 8,586,629 B2    11/2013    De Groote

OTHER PUBLICATIONS

Oman O.M. in Ultrastructural Nephropathy 38(1):26-33 (2014).*
Kanter, M. in Journal of Molecular Hostology 40:107-115 (2009).*
Goodman and Gilman's The Pharmacological Basis of Therapeutics (Tenth Edition (2001), McGraw Hill, Chapter I, pp. 3-29.*
Sayed A.A. in European Review for Medical and Pharmacological Sciences, 16:808- 815 (2012).*
Lu et al. in Journal of Clinical and Experimental Opthalmology 5:4, 1-9 (2014).*
Kowluru et al. in Experimental Diabetes Research, vol. 2007, 12 pages.*
Kern et al. in Diabetes 56:373-379, 2007.*
Erdurmus et al. in Cornea 26(6) 715-719 (2007) (Abstract).*

* cited by examiner

*Primary Examiner* — Dennis Heyer
(74) *Attorney, Agent, or Firm* — Richard C. Litman; Nath, Goldberg & Meyer

(57) ABSTRACT

A method of preventing and/or treating a disease caused by diabetes complications includes administering to a patient in need thereof, an effective amount of thymoquinone or a pharmaceutically acceptable salt thereof, either singly or in combination with a pharmaceutically acceptable carrier, diluent or excipient. The disease can be at least one of retinopathy, nephropathy, neuropathy, and neurological disorder.

3 Claims, 3 Drawing Sheets

METHOD FOR TREATING A NEUROVASCULAR COMPLICATION OF DIABETES MELLITUS

BACKGROUND OF THE INVENTION

1. Field of the Invention

The invention relates generally to a method of treating or preventing the complications associated with diabetes mellitus, especially neurovascular complications, using thymoquinone (TQ).

2. Description of the Related Art

Diabetes mellitus (DM) is characterized by hyperglycemia (high glucose in the blood), which results either from insufficient production of insulin (type 1 diabetes) or from a cellular insensitivity to insulin in the blood. Diabetes mellitus is a growing chronic disease that adversely affects the lives of millions of people around the world, and is among the major causes of death especially in developed countries. It has been a most distressing disease that can develop to a seriously life threatening condition. The effects of diabetes mellitus include long-term damage, dysfunction and failure of various organs. The main associated complications include cardiovascular disease, nephropathy, retinopathy, neuropathy lead to disability, and reduced life expectancy.

Diabetic retinopathy (DR) is a slow progressive retinal disease and occurs as a consequence of long-standing accumulated functional and structural impairment of the retina by diabetes. The cause of vision loss in DR is multi-factorial and remains unknown. Recently, early retinal neurodegeneration was suggested to play a key role in the development of DR. Features of DR include increased retinal vascular permeability, loss of neurotropic support and apoptosis.

The global prevalence of DM continues to increase and is highest in the Middle East. The overall crude prevalence of type two DM (T2DM) in the Kingdom of Saudi Arabia (KSA) is 21.3-23.7% with an age-adjusted prevalence of 21.9-31.6%. The economic burden of diabetes is growing worldwide. The average healthcare cost for patients with diabetes is 2-4 times that of non-diabetics where the major component of the direct cost (estimated to be >80%) is related to hospitalization, mainly resulting from chronic albeit preventable complications. The global healthcare expenditures on diabetes alone is projected to amount from US$376 billion in 2010 to US$490 billion in 2030. The estimated annual medical cost of diabetes care in Saudi Arabia is enormous and could amount to Saudi Riyal 15-25 billion.

Currently, no drug has been particularly proven to ameliorate the neurovascular complications of diabetes. Therefore, it would be desirable to find a breakthrough drug in the management of complications of DM, especially neurovascular complications such as retinopathy.

Thus, a method of treating and preventing neurovascular complication of diabetes mellitus solving the aforementioned problem is desired.

SUMMARY OF THE INVENTION

A method of preventing and/or treating neurovascular complications of diabetes mellitus includes administering to a patient in need thereof, an effective amount of thymoquinone or a pharmaceutically acceptable salt thereof, either singly or in combination with a pharmaceutically acceptable carrier, diluent or excipient. The disease can be at least one of retinopathy, nephropathy, neuropathy, and neurological disorder.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
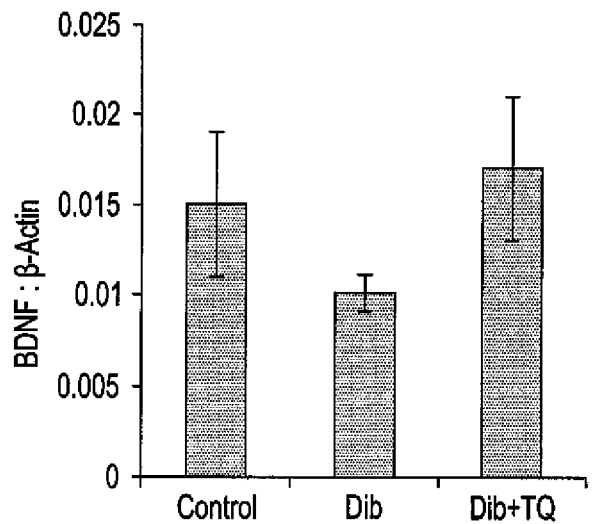
FIGS. 1A-1D is a graph showing retinal expression of mediators and markers of neurodegeneration in diabetic retinas, nondiabetic controls, and thymoquinone treated diabetic retinas.

A method for treating and/or preventing neurovascular complications of diabetes mellitus includes administering to a patient in need thereof, an effective amount of thymoquinone or a pharmaceutically acceptable salt thereof, either singly or in combination with a pharmaceutically acceptable carrier, diluent or excipient. Neurovascular complications of diabetes mellitus can include, for example, retinopathy, nephropathy, neuropathy, and neurological disorder.

Diabetic retinopathy is a complication of the retina caused by diabetes that involves damage and degeneration to the tiny blood vessels in the back of the eye (retina). Features of diabetic retinopathy include increased retinal vascular permeability, loss of neurotropic support and apoptosis. The present inventors have evaluated the putative modulatory role of thymoquinone in hyperglycemia-induced alteration in metabolic functions of retina causing blood retina barrier (BRB) alterations and vascular neurodegeneration. A measure of ROS generation is indicative of whether thymoquinone treatment is working to reduce diabetic neurovascular complications and more specifically diabetes-induced BRB breakdown. Initial BRB breakdown is associated not only with increases in reactive oxygen species (ROS) but also the expression of both the endothelial and neuronal nitric oxide synthase (eNOS and nNOS) as well as increases in vascular endothelial growth factor (VEGF) expression, causing pathological neovascularization. The present inventors found that thymoquinone (TQ) significantly attenuates the effect of diabetes on the neurovascular events of the retina and that thymoquinone controls diabetes-induced neurovascular changes even under high serum glucose levels.

Thymoquinone has multiple actions including anti-inflammatory and immunoregulatory effects. The present inventors analyzed the ROS as an inducer of vascular permeability. The present inventors found neuroprotective support of thymoquinone in diabetic retinal neurodegeneration. Furthermore, the present inventors found attenuation of diabetes induced cleaved caspase-3, the apoptosis executor enzyme. Therefore, it is believed that thymoquinone exerts its effect through various pathways for treating and/or preventing the neurovascular complications of diabetes, in general, and retinopathy, in particular.

Thymoquinone is a phytochemical compound found in the plant *Nigella sativa*. The IUPAC name of thymoquinone is 2-Isopropyl-5-methylbenzo-1,4-quinone. Its structure is provided below.

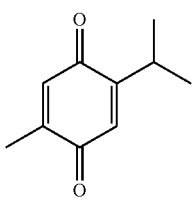

Thymoquinone can be administered as it is, or as a tautomer, an analogue, a derivative, an acceptable salt form or as a pharmaceutical formulation or composition thereof with a pharmaceutically acceptable carrier, to a patient to prevent, treat or development-inhibit simple retinopathy or preproliferative retinopathy. The patient can be a mammal e.g., men, mice, rats, rabbits, dogs, cats, bovines, pigs, monkeys, etc.

Examples of pharmaceutically acceptable carriers include various organic or inorganic carriers which are generally used in this field. For example, an excipient, a lubricant, a binder, a disintegrating agent, etc. are used in the solid formulations, and a solvent, a solubilizer, a suspending agent, an isotonizing agent, a buffer, a soothing agent, etc. are used in the liquid formulations. In addition, if desired, an appropriate additive such as a preservative, an antioxidant, a colorant, a sweetener, etc. may be used in the above formulations.

Examples of an excipient include lactose, sucrose, D-mannitol, D-sorbitol, starch, α-starch, dextrin, crystalline cellulose, hydroxypropyl cellulose with a low degree of substitution, sodium carboxymethyl cellulose, gum arabic, dextrin, pullulan, light silic acid anhydride, synthesized aluminium silicate, magnesium aluminate metasilicate, etc. Examples of a lubricant include magnesium stearate, calcium stearate, talc, colloidal silica, etc. Examples of a binder include α-starch, cane sugar, gelatine, gum arabic, methyl cellulose, carboxymethyl cellulose, sodium carboxymethyl cellulose, crystalline cellulose, sucrose, D-mannitol, trehalose, dextrin, pullulan, hydroxypropyl cellulose, hydroxypropylmethyl cellulose, polyvinyl-pyrrolidone, etc. Examples of a disintegrating agent include lactose, sucrose, starch, carboxymethyl cellulose, carboxymethyl cellulose calcium, croscarmellose sodium, sodium carboxymethyl starch, light silic acid anhydride with a low degree of substitution, hydroxypropyl cellulose, etc. Examples of a solvent include water for injection, Ringer solution, alcohol, propyleneglycol, polyethyleneglycol, sesame oil, corn oil, olive oil, cotton seed oil, etc. Examples of a solubilizer include polyethyleneglycol, propyleneglycol, D-mannitol, trehalose, benzyl benzoate, ethanol, trisaminomethane, cholesterol, triethanolamine, sodium carbonate, sodium citrate, sodium salicylate, sodium acetate, etc. Examples of a suspending agent include surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc.; polysorbates, polyoxyethylene hardened castor oil, etc.

Examples of an isotonizing agent include sodium chloride, glycerin, D-mannitol, D-sorbitol, glucose, etc. Examples of a buffer include a buffer solution of phosphate, acetate, carbonate, citrate, etc. Examples of a soothing agent include benzylalcohol, etc. Examples of a preservative include paraoxybenzoic acid esters, chlorobutanol, benzyl- alcohol, phenethylalcohol, dehydroacetic acid, sorbic acid, etc. Examples of the antioxidant include sulfites, ascorbic acid, etc. Preferable examples of colorants include water-soluble synthetic organic food additives (e.g., food dyes such as food red dye Nos. 2 and 3, food yellow dye Nos. 4 and 5 and food blue dye Nos. 1 and 2), water-insoluble lake dyes (e.g., aluminium salts of the above water-soluble synthetic organic food additives, etc.), natural pigments (e.g., β-carotene, chlorophyll, iron oxide red, etc.), etc. Preferable examples of edulcorants include sodium saccharate, glycyrrhizin dipotassium, aspartame, Stevia, etc.

The term "effective amount," as used herein and in the claims, refers to an amount of thymoquinone or a pharmaceutically acceptable salt thereof sufficient to prevent, ameliorate, treat and/or lessen the damage caused by a neurovascular complication of diabetes mellitus, such as diabetic retinopathy.

The pharmaceutical composition is orally or parenterally administered in safety in the form of, for example, orally administered compositions such as tablets, capsules (including soft capsules and microcapsules), granules, powders, syrups, emulsions, suspensions, etc.; and parenterally administered compositions such as injections (e.g., subcutaneous injection, intravenous injection, intramuscular injection, intraperitoneal injection, intravitreous injection, injections to the eyeball and the retina, etc.), drops, medicines for external use (e.g., nasotracheally administered compositions, percutaneously administered compositions, ointments, etc.), suppositories (e.g., rectal suppository, vaginal suppository, etc.), pellets (e.g., pellets for indwelling on retina, etc.), drops, ophthalmic topically administered compositions (e.g., eye drops, ophthalmic ointment, etc.) and the like.

The pharmaceutical composition can be prepared according to any of the conventional methods in the field of pharmaceutical compositions. For example, a pharmaceutical composition to be orally administered is prepared by adding to the active ingredient an excipient (e.g., lactose, sucrose, starch, D-mannitol, etc.), disintegrating agent (e.g., carboxymethyl cellulose calcium, etc.), binder (e.g., α-starch, gum arabic, carboxymethyl cellulose, hydroxypropyl cellulose, polyvinyl-pyrrolidone, etc.), lubricant (e.g., talc, magnesium stearate, polyethyleneglycol 6000, etc.), etc., and compression-molding the mixture composition, and if necessary, coating the composition with a coating base material by a known method so as to mask the taste or allow the composition to dissolve in the intestine or to have persistence. Examples of the coating base material include sugar coating material, water-soluble film coating material, enteric film coating material, sustained release film coating material, etc. As the sugar coating material, saccharose is used, which may be used in combination with at least one selected from talc, precipitated calcium carbonate, gelatin, gum arabic, pullulan, carnauba wax, etc.

Examples of the water-soluble film coating material include cellulose polymers such as hydroxypropyl cellulose, hydroxypropylmethyl cellulose, hydroxyethyl cellulose, and methyl hydroxyethyl cellulose; synthesized polymers such as polyvinyl acetal diethylaminoacetate, aminoalkylmethacrylate copolymer E [Eudragit E (trade name), Rhom Pharma], polyvinyl-pyrrolidone, etc.; polysaccharides such as pullulan, etc. Examples of the enteric film coating material include cellulose polymers such as hydroxypropylmethyl cellulose phthalate, hydroxypropylmethyl cellulose acetate succinate, carboxymethylethyl cellulose, cellulose acetate phthalate, etc.; acrylic polymers such as methacrylate copolymer LD [Eudragit L-30D55 (trade name), Rhom Pharma], methacrylic copolymer S [Eudragit S (trade name), Rhom Pharma]; and natural substances such as shellac, etc. Examples of the sustained release film coating materials include cellulose polymers such as ethyl cellulose; and acrylate polymers such as aminoalkyl methacrylate copolymer RS[Eudragit RS (trade name), Rhom Pharma], ethyl acrylate, methyl methacrylate copolymer suspension [Eudragit NE (trade name), Rhom Pharma], etc. Each of the coating materials may be used as a mixture with at least two thereof in a proper ratio. In addition, a light-shielding material such as titanium oxide, iron sesquioxide or the like may be used in the course of coating.

The injection is prepared by dissolving, suspending or emulsifying the active ingredient in an aqueous solvent (e.g., distilled water, physiological salt solution, Ringer solution, etc.), an oil solvent (e.g., vegetable oils such as olive oil, sesame oil, cotton seed oil, corn oil, and propyleneglycol, etc.) or the like in the presence of a dispersant (e.g., polysorbate 80, polyoxyethylene hardened castor oil 60, etc.), polyethyleneglycol, carboxymethyl cellulose, sodium alginate, etc.), preservative (e.g., methyl paraben, propyl paraben, benzylalcohol, chlorobutanol, phenol, etc.), isotonizing agent (e.g., sodium chloride, glycerin, D-mannitol, D-sorbitol, glucose, etc.) or the like. In this preparation, if necessary, additives such as a solubilizer (e.g., sodium salicylate, sodium acetate, etc.), stabilizer (e.g., human serum albumin, etc.), soothing agent (e.g., benzylalcohol, etc.) and the like may be used.

Preferable examples of the ophthalmic topical agent include eye drops, ophthalmic ointment, etc., and the eye drops may be of aqueous or non-aqueous and in the form of a solution or a suspension. Further, the compound may be dispersed in or adsorbed onto an ophthalmic ointment, gel or a sustained release polymer for use in the composition.

The aqueous eye drops may contain conventional additives such as an isotonizing agent, buffer, pH-adjusting agent, preservative, chelating agent and the like. Examples of the isotonizing agent include sodium chloride, mannitol, sorbitol, glycerin, etc.; examples of the buffer include phosphate, borate, acetate, citrate, etc.; examples of the pH-adjusting agent include hydrochloric acid, acetic acid, sodium hydroxide, etc.; examples of the preservative include paraoxybenzoic acid esters, benzalkonium chloride, chlorohexydine, benzylalcohol, sorbic acid, or a salt thereof, thiomerosal, chlorobutanol, etc.; and examples of the chelating agent include sodium edetate, sodium citrate, condensed sodium phosphate, etc.

The aqueous eye drops may further contain a thickener or/and a suspending agent, examples of which include methyl cellulose, carmellose or a salt thereof, hydroxyethyl cellulose, sodium alginate, carboxyl vinyl polymer, polyvinylalcohol, polyvinylpyrrolidone, etc. Further, the aqueous eye drops may contain a surfactant (e.g., polyethyleneglycol, propyleneglycol, polyoxyethylene hardened castor oil, polysorbate 80, etc.), etc. When the compound is administered in the form of an aqueous suspending eye drops, the polymer thickener, surfactant and the like may be suitably selected for use in the composition.

When the compound is administered in the form of non-aqueous eye drops, the solvent therefor is suitably selected from vegetable oils such as castor oil, sesame oil, soybean oil and olive oil, and liquid paraffin, propyleneglycol, β-octyldodecanol and the like for use in the composition. When the compound is administered in the form of non-aqueous suspending eye drops, the solvent therefor is suitably selected from thixotropic colloids such as aluminium monostearate and the like for use in the composition. The pH of the eye drops is adjusted within a range for conventional eye drops, generally 4.0 to 9.0, preferable 5.0 to 8.0.

When the compound is administered in the form of an ophthalmic ointment, the base material therefor is suitably selected from vaseline, plastibase, liquid paraffin and the like for use in the composition. The base material as the gelling agent of the eye drops is suitably selected from, for example, a carboxyl vinyl polymer, methyl cellulose, sodium alginate, hydroxypropyl cellulose, ethylene maleic anhydride polymer and the like for use in the composition.

According to one embodiment, thymoquinone or a pharmaceutically acceptable salt thereof can be administered in a dose form of about 2 mg/kg every other day (or about 0.5-1 mg/kg daily) to the patient suffering from neurovascular complications of diabetes mellitus. The thymoquinone or a pharmaceutically acceptable salt thereof can be administered orally, topically, rectally, or by injection.

The following examples describe tests conducted to evaluate thymoquinone as a drug candidate for the treatment and prevention of the complications of diabetes mellitus and should be construed as exemplary only.

Healthy Sprague Dawley rats (150-200 g) were used for the trials. Animals were issued from Central Animal House Facility of the College of Pharmacy, King Saud University and were kept in standard plastic animal cages in groups of 6 animals each with 12 hours light and dark cycle at 25±2° C. The rats were fed on standard rat chow and provided water ad libitum. The animals were acclimatized to laboratory conditions for a week prior to experiments. Diabetes was induced in overnight fasted rats by administration of Streptozotocin (STZ) at dose of 55 mg/kg intraperitoneally in citric acid buffer (pH 4.5). After one hour of STZ administration, the animals were allowed to feed ad libitum. The animals were kept under observation and fasting blood glucose levels were estimated before 72 hours of STZ treatment. Animals showing blood glucose levels >350 mg/dl were considered as diabetic and were used for further trials. Diabetic rats were divided into two groups (10 rats per group) at random. Group I served as diabetic control. Group II were administered thymoquinone (2 mg/kg intraperitoneally) in alternate days for three weeks. Healthy rats were also kept as normal controls. Relevant biochemical parameters including serum creatinine, uric acid, alanine aminotransferase (ALT), aspartate aminotransferase (AST), alkaline phosphatase and bilirubin were assessed using colorimetric methods.

Example 1

Western Blot Assay

Following animal euthanasia, rats' retinas were collected and homogenized in a Western lysis buffer (30 mM Tris-HCl, pH 7.4, 250 mM $Na_3VO_4$, 5 mM EDTA, 250 mM sucrose, 1% Triton X-100 with Protease inhibitor). The lysate was centrifuged at 14,000×g for 10 min at 4° C. and the supernatant was collected. Protein content was assayed by DC protein assay. The tissue lysates containing 40-50 μg protein were separated on 10-15% SDS-polyacrylamide gels and were transferred onto nitrocellulose membranes. The blots were blocked with 5% nonfat milk in TBS-T buffer (20 mM Tris-HCl, pH 7.6, 136 mM NaCl, and 0.1% Tween-20).

For detection of brain derived neurotrophic factor (BDNF), tyrosine hydroxylase (TH), nerve growth factor receptor (NGFR), and cleaved caspase-3, the membrane was incubated overnight at 4° C. with mouse monoclonal anti- BDNF (1:500) mouse monoclonal anti-tyrosine hydroxylase (1:300), Mouse monoclonal anti-Human NGF R (1:500) and rabbit monoclonal anti-caspase-3 (1:300). After overnight incubation with primary antibodies, the membranes were washed four times with TBS-T (5 min each). For BDNF, TH, NGFR measurements, the membrane was incubated at room temperature for 1.5 hours with anti-mouse secondary horseradish peroxidase-conjugated antibody (1:2000, SC-2005, Santa Cruz Biotechnology), and for cleaved caspase-3, with anti-rabbit secondary horseradish peroxidase-conjugated antibody (1:2000). After incubations with secondary antibodies, membranes were washed four times with TBS-T (5 min each) and the immunoreactivity of bands was visualized on a high-performance chemiluminescence machine by using enhanced chemiluminescence plus Luminol and quantified by densitometric analysis using image processing and analysis in GeneTools. As a control, the blots were stripped and detected with a mouse monoclonal anti-β-actin antibody (1:2000). All data from the three independent experiments were expressed as a ratio to the optical density (OD).

Example 2

Reactive Oxygen Species (ROS) Measurements

Reactive Oxygen Species (ROS) generation was measured in retinal tissue homogenates using a 2',7'-dichlorofluorescein-diacetate (DCHFDA) as is known in the art. DCFHDA, a nonfluorescent dye, was cleaved by esterase activity to yield DCFH (2',7'-dichlorofluorescein), which was subsequently oxidized by a variety of ROS to form diehlorofluorescein (DCF), which is fluorescent. Retinas were homogenized in PBS in the presence of protease inhibitor using a glass homogenizer. Samples containing 20 m proteins diluted in PBS were incubated with 5 μM DCFHDA (Invitrogen, CA, USA) in the dark for 15 min. Fluorescence was measured using a SpectraMax Gemini-XPS every 15 min for 1 hour with excitation and emission wavelengths of 488 nm and 525 nm, respectively.

Example 3

Measurement of Blood Retinal Barrier (BRB) Breakdown

Rat retinas were analyzed for Blood Retinal Barrier (BRB) breakdown after 3 weeks of thymoquinone dosing using fluorescein isothiocyanate (FITC)-conjugated dextran as previously described in the prior art. Briefly, rats were deeply anesthetized and then FITC-conjugated dextran (40 kDa) was injected intravenously (50 mg/kg body weight). After 10 to 15 min, a blood sample was collected and each rat was then perfused with Phosphate Buffer Saline (PBS). After perfusion, the retinas were carefully removed, weighed and homogenized to extract the FITC conjugated dextran. Fluorescence was measured using a Spectra Max Gemini-XPS with excitation and emission wavelengths of 485 nm and 538 nm, respectively, with PBS as a blank. Blood retinal barrier breakdown was calculated using the following equation (1) with the results being expressed in μL $g^{-1}$ $hr^{-1}$.

$$\frac{\text{Retinal } FITC\text{-dextran } (\mu g)/\text{retinal weight } (g)}{\text{Plasma } FITC\text{-dextran concentration } (\mu G/\mu L) * (\text{circulation time (hr)})} \quad (1)$$

After three weeks of induction of diabetes with a single high-dose of STZ, the body weights of the diabetic rats were lower and their blood glucose levels were more than four-fold higher compared with age-matched normal control rats as shown in Table 1.

TABLE 1

Glucose Concentration in Diabetic Rats with and without Thymoquinone (TQ) Administration

| Thymoquinone TQ Treatment | Normal Control | Diabetic Rats Group II Diabetic Control Glucose Concentration (mg/dl) | Diabetic Rats Group III TQ 2 mg/Kg Glucose Concentration (mg/dl) |
|---|---|---|---|
| After 7 days of TQ treatment | 86.08 ± 1.46 | >600 | 580.58 ± 2.40 |
| After 14 days of TQ treatment | 85.82 ± 1.80 | >600 | 559.55 ± 1.29 |
| After 21 days of TQ treatment | 85.00 ± 2.10 | >600 | 495.10 ± 5.71 |

The diabetic rats that received thymoquinone exhibited more normal kidney and liver function tests than untreated animals as provided in Table 2.

TABLE 2

Bio Effect of Diabetes and Thymoquinone Treatment of Kidney and Liver Functions

|  | Normal Control | Diabetic Control | Treated TQ (2 mg/kg) |
|---|---|---|---|
| ALT (U/l) | 49.43 ± 3.49 | 240.29 ± 6.66 | 134.43 ± 5.21 |
| AST (U/l) | 141.35 ± 4.63 | 255.88 ± 3.54 | 138.48 ± 2.94 |
| ALKALINE Phos (U/l) | 100.7 ± 3.66 | 230.81 ± 5.29 | 179.08 ± 4.51 |
| Bilirubin (mg/dl) | 3.00 ± 0.04 | 5.10 ± 0.05 | 3.23 ± 0.04 |
| Creatinine (mg/dl) | 0.48 ± 0.03 | 0.86 ± 0.04 | 0.62 ± 0.05 |
| Uric acid (mg/dl) | 2.80 ± 0.06 | 6.73 ± 0.14 | 4.99 ± 0.07 |

Figure 1B:
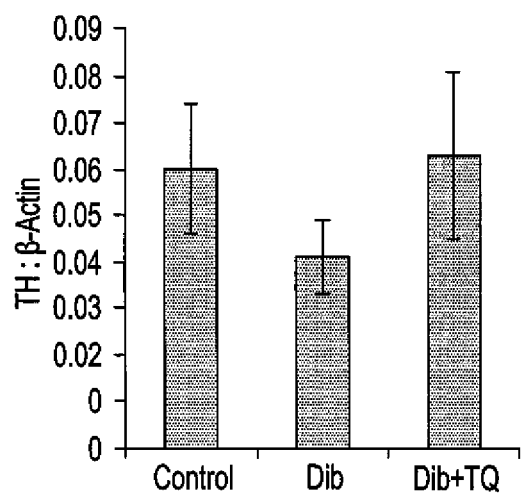
Figure 1C:
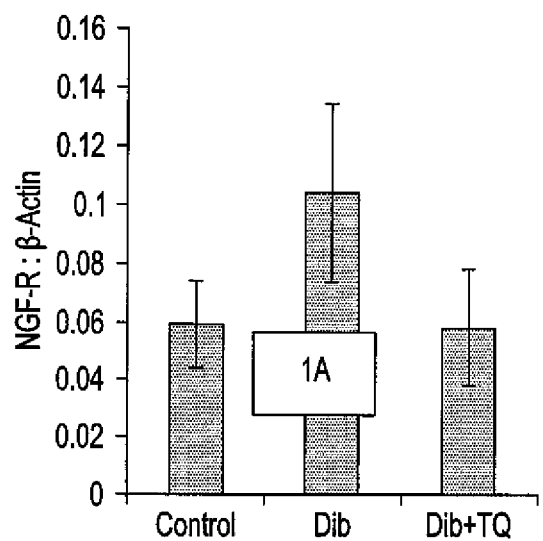
Figure 1D:
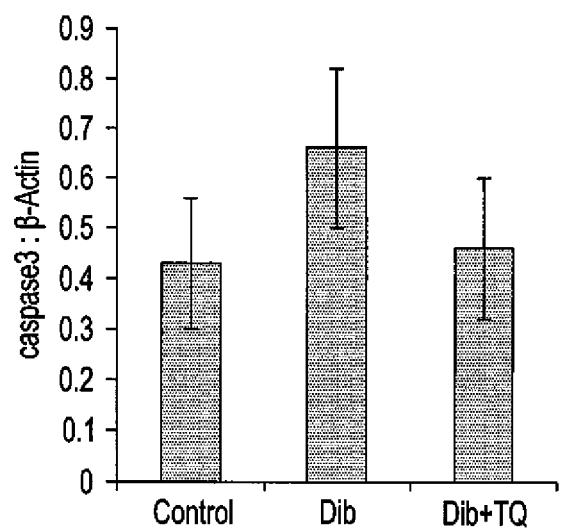

The effect of diabetes on retinal expression of mediators and markers of neurodegeneration is illustrated in FIGS. 1A-1D. As shown in FIG. 1A, the neurotrophin BDNF was significantly down-regulated (about 65%) in diabetic retinas as compared with nondiabetic controls. The dopaminergic amacrine cell marker TH levels obtained in diabetic animals were also significantly lower than those of nondiabetic animals. The levels decreased by about 32% as shown in FIG. 1B. Diabetes significantly increased NGFR expression in the retinas by about 75% as shown in FIG. 1C. Furthermore, cleaved caspase-3, the apoptosis executor enzyme was significantly up-regulated (about 52%) in diabetic retinas compared with nondiabetic controls as shown in FIG. 1D. All of these changes were normalized by thymoquinone treatment in diabetic rats.

Figure 2:
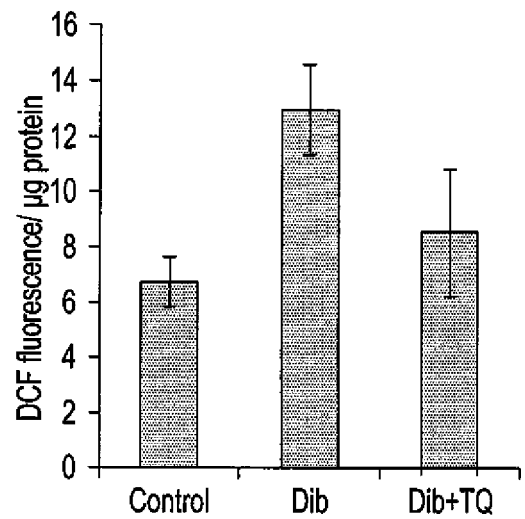
FIG. 2 is a graph showing the effect of thymoquinone on ROS production in retinas of diabetic animals.

In order to assess whether thymoquinone (TQ) reduces diabetes-induced BRB breakdown through a reduction in ROS generation, DCF retinal levels were measured as a marker for reactive oxygen species (ROS). As shown in FIG. 2, the ROS generation in diabetic animals treated with thymoquinone was significantly attenuated. Oxidative stress plays an important role in retinal vascular endothelial dysfunction in diabetes. Compared with the retina of nondiabetic animals, the retina of diabetic animals demonstrated a 90% increase in ROS generation.

Figure 3:
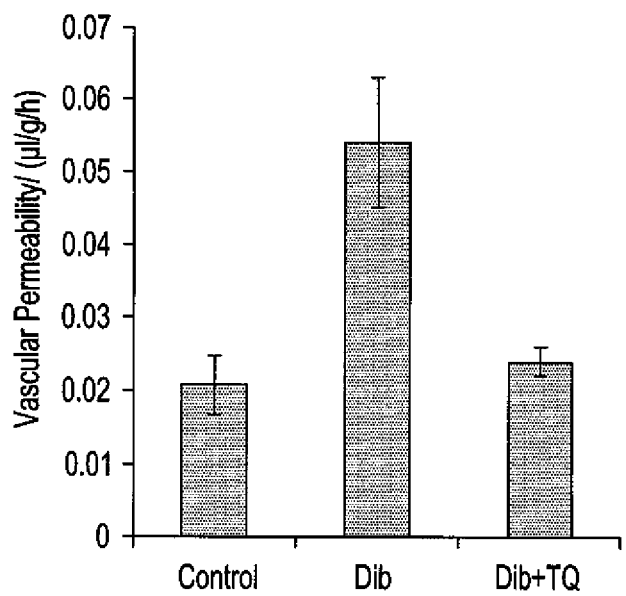
FIG. 3 shows the effect of thymoquinone (TQ) on Blood-Retinal Barrier Breakdown in Streptozotocin (STZ)-Induced Diabetic Rats.

The effect of thymoquinone (TQ) on Blood-Retinal Barrier Breakdown in STZ-Induced Diabetic Rat was further evaluated. Fluorescein isothiocyanate (FITC)-conjugated dextran was used to determine the extent of vascular permeability. In STZ-diabetic rats, the retinal vascular permeability was significantly increased by more than two-fold when compared with nondiabetic rats. As illustrated in FIG. 3, treatment with thymoquinone (2 mg/kg on alternate days) significantly attenuated the effect of diabetes on BRB breakdown when compared with diabetic retinas.

It is to be understood that the present invention is not limited to the embodiments described above, but encompasses any and all embodiments within the scope of the following claims.

We claim:

1. A method of treating a neurovascular complication of diabetes mellitus causing alterations in blood retina barrier (BRB) and vascular neurodegeneration, comprising: diagnosing the neurovascular complication of diabetes mellitus as being at least retinopathy;

administering to a patient in need thereof about 2 mg/kg of thymoquinone (TQ) or a pharmaceutically acceptable salt thereof every other day; and measuring at least the reactive oxygen species (ROS) and vascular endothelial growth factor (VEGF) throughout the administration of the TQ and analyzing the alterations in the BRB.

2. The method of treating a neurovascular complication of diabetes mellitus according to claim 1, wherein the thymoquinone or a pharmaceutically acceptable salt thereof is administered topically, enterally, or parenterally.

3. A method of treating a neurovascular complication of diabetes mellitus causing alterations in blood retina barrier (BRB) and vascular neurodegeneration, comprising: diagnosing the neurovascular complication of diabetes mellitus as being at least retinopathy;

administering to a patient in need thereof about 2 mg/kg of thymoquinone (TQ) or a pharmaceutically acceptable salt thereof every other day; and measuring at least the reactive oxygen species (ROS) and vascular endothelial growth factor (VEGF) throughout the administration of the TQ and analyzing the alterations in the BRB.

* * * * *